United States Patent
Picard et al.

(10) Patent No.: US 10,833,368 B2
(45) Date of Patent: Nov. 10, 2020

(54) ELECTROLYTE FOR ELECTROCHEMICAL GENERATOR

(71) Applicant: COMMISSARIAT A L'ENERGIE ATOMIQUE ET AUX ENERGIES ALTERNATIVES, Paris (FR)

(72) Inventors: Lionel Picard, Seyssinet-pariset (FR); Gerard Gebel, Saint-Egreve (FR); Melody Leclere, La-batie-Montgascon (FR); Hakima Mendil, Vitry sur Seine (FR); Patrice Rannou, Eybens (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 273 days.

(21) Appl. No.: 15/761,257

(22) PCT Filed: Sep. 20, 2016

(86) PCT No.: PCT/EP2016/072312
§ 371 (c)(1),
(2) Date: Mar. 19, 2018

(87) PCT Pub. No.: WO2017/050769
PCT Pub. Date: Mar. 30, 2017

(65) Prior Publication Data
US 2018/0261886 A1  Sep. 13, 2018

(30) Foreign Application Priority Data
Sep. 21, 2015 (FR) .................................... 15 58864

(51) Int. Cl.
*H01M 10/056* (2010.01)
*H01M 10/0569* (2010.01)
(Continued)

(52) U.S. Cl.
CPC ....... *H01M 10/0569* (2013.01); *C07C 309/47* (2013.01); *C07C 309/76* (2013.01);
(Continued)

(58) Field of Classification Search
CPC .. C07C 309/47; C07C 309/76; H01M 10/052; H01M 10/0525; H01M 10/0564; H01M 10/0569
See application file for complete search history.

(56) References Cited

U.S. PATENT DOCUMENTS 9,573,887 B2 * 2/2017 Kakizuka ............... C07C 309/47
2002/0047104 A1  4/2002 Igawa et al.
(Continued)

FOREIGN PATENT DOCUMENTS

EP  1 176 184 A2  1/2002
EP  2 792 671 A1  10/2014
(Continued)

OTHER PUBLICATIONS

Machine translation of JP 03-164737 (no date).*
(Continued)

*Primary Examiner* — Amanda C. Walke
(74) *Attorney, Agent, or Firm* — Oblon, McClelland, Maier & Neustadt, L.L.P.

(57) ABSTRACT

Thermotropic ionic liquid crystal molecules, comprising a so-called rigid part, a so-called flexible part bonded covalently, directly or via a spacer, to said rigid part, and one or more ionic groups bonded covalently to said rigid part. Said molecules can be used as electrolytes in an electrochemical device, in particular a lithium-ion battery.

25 Claims, 5 Drawing Sheets

Figure 1:
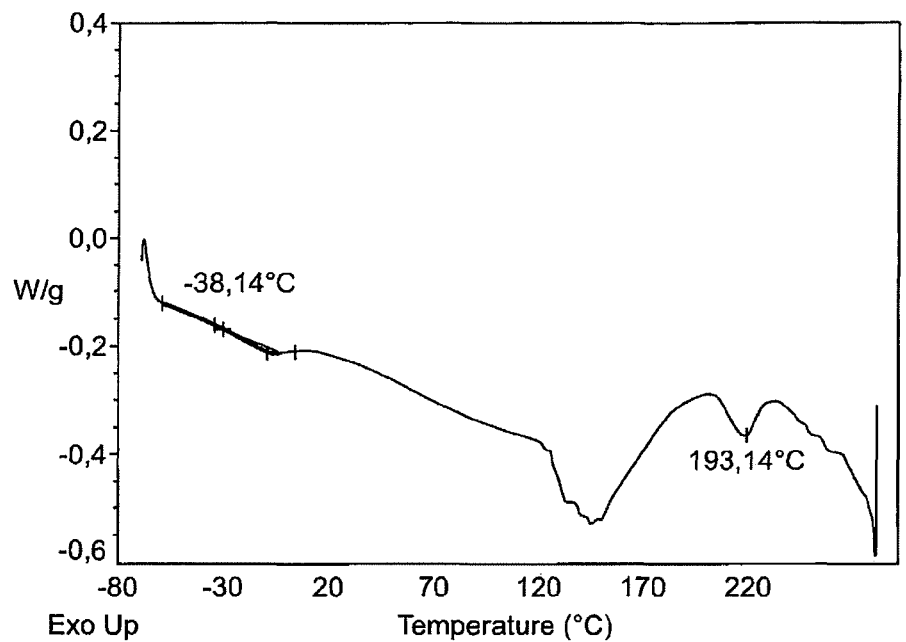

(51) Int. Cl.

| | | |
|---|---|---|
| *C25B 9/00* | (2006.01) | |
| *C09K 19/32* | (2006.01) | |
| *C07C 309/47* | (2006.01) | |
| *H01M 10/0564* | (2010.01) | |
| *H01M 10/052* | (2010.01) | |
| *C07C 309/76* | (2006.01) | |
| *H01M 10/0525* | (2010.01) | |
| *H01M 8/1018* | (2016.01) | |

(52) U.S. Cl.
CPC ............ *C09K 19/32* (2013.01); *C09K 19/322* (2013.01); *C25B 9/00* (2013.01); *H01M 10/052* (2013.01); *H01M 10/0525* (2013.01); *H01M 10/0564* (2013.01); *C09K 2019/328* (2013.01); *H01M 2008/1095* (2013.01); *H01M 2300/0025* (2013.01); *H01M 2300/0028* (2013.01); *H01M 2300/0034* (2013.01)

(56) References Cited

U.S. PATENT DOCUMENTS

| | | | | |
|---|---|---|---|---|
| 2012/0129045 | A1* | 5/2012 | Gin | ........................ H01B 1/122 |
| | | | | 429/189 |
| 2014/0336414 | A1 | 11/2014 | Kato et al. | |
| 2016/0329541 | A1* | 11/2016 | Adams | ................ H01M 2/1686 |

FOREIGN PATENT DOCUMENTS

| | | | |
|---|---|---|---|
| FR | 2 979 630 A1 | 3/2013 | |
| JP | 03164737 A * | 7/1991 | |
| JP | 2000-336052 A | 12/2000 | |
| WO | WO-9843953 A1 * | 10/1998 | .......... C07C 229/70 |
| WO | WO 00/05774 A1 | 2/2000 | |

OTHER PUBLICATIONS

English language Written Opinion of WO 2017/050769 (no date).*
International Search Report dated Nov. 11, 2016 in PCT/EP2016/072312 (with English translation), citing documents AA, AB, AO—AQ and AW—AY therein, 6 pages.
Rachid Meziane, et al. "Single-Ion Polymer Electrolytes Based on a Delocalized Polyanion for Lithium Batteries" Electrochimica Acta, Elsevier, vol. 57, 2011, pp. 14-19.
Morrel H. Cohen, et al. "Molecular Transport in Liquids and Glasses" The Journal of Chemical Physics, vol. 31, No. 5, Nov. 1959, pp. 1164-1169 and cover page.
Takahiro Ichikawa, et al., "Induction of Thermotropic Bicontinuous Cubic Phases in Liquid-Crystalline Ammonium and Phosphonium Salts" Journal of the American Chemical Society, vol. 134, No. 5, XP055288958, Jan. 9, 2012 pp. 2634-2643.
Takahiro Ichikawa, et al., "3D Interconnected Ionic Nano-Channels Formed in Polymer Films: Self-Organization and Polymerization of Thermotropic Bicontinuous Cubic Liquid Crystals" Journal of the American Chemical Society, vol. 133, No. 7, XP055288963, Jan. 27, 2011, pp. 2163-2169.
Junji Sakuda, et al., "Liquid-Crystalline Electrolytes for Lithium-Ion Batteries: Ordered Assemblies of a Mesogen-Containing Carbonate and a Lithium Salt" Advanced Functional Materials, vol. 25, No. 8, XP001595313, Feb. 25, 2015 pp. 1206-1212.
U.S. Appl. No. 15/761,305, filed Mar. 19, 2018, Leclere, et al.

* cited by examiner

ELECTROLYTE FOR ELECTROCHEMICAL GENERATOR

The present invention relates to novel compounds that can be used as electrolytes, especially in electrochemical storage or generation systems.

Such electrolytes may be used in various electrochemical systems or devices, especially in lithium batteries.

Conventionally, the operating principle of an electrochemical generator is based on the insertion and removal, also known as "deinsertion", of an alkali metal ion or of a proton into and from the positive electrode, and the deposition or extraction of this ion onto and from the negative electrode.

The main systems use the lithium cation as the ionic transport species. In the case of a lithium accumulator, for example, the lithium cation extracted from the cathode during charging of the battery becomes deposited on the anode, and, conversely, it is extracted from the anode to be intercalated in the cathode during discharging.

Transport of the proton or of the alkali or alkaline-earth metal cation, in particular the lithium ion, between the cathode and the anode is ensured by an ion-conducting electrolyte.

The formulation of the electrolyte used is an essential factor for the performance of the electrochemical system, in particular when said system is used at very low or very high temperatures. The ion conductivity of the electrolyte in particular conditions the efficiency of the electrochemical system, given that it has an influence on the mobility of the ions between the positive and negative electrodes.

Other parameters also have an influence on the choice of the electrolyte used. The factors concerned are especially its thermal, chemical or electrochemical stability in the electrochemical system, and also economic, safety and environmental protection criteria, especially including the toxicity of the electrolyte.

In general, the electrolytes of electrochemical systems are in liquid, gelled or solid form.

As regards electrolytes in liquid form, the conventional electrolytes of electrochemical generators with a metal cation from one of the first two columns of the Periodic Table of the Elements, for example lithium, are composed of a salt of this cation dissolved in an organic or aqueous medium (conventionally in carbonate solvents or acetonitrile for lithium batteries), in the presence or absence of additives.

For example, conventional supercapacitor electrolytes are composed of an organic salt (conventionally a tetraethylammonium tetrafluoroborate salt $Et_4N$—$BF_4$) dissolved in acetonitrile.

Their use as a complete electrochemical storage system, for example in an Li-ion battery, makes it necessary, however, to add a separator in order to ensure electrical insulation between the positive and negative electrodes. Also, although these electrolytes have good ion conductivities, they however have safety and cost problems in the context of using organic solvents (low thermal stability), and electrochemical stability problems in the context of use of an aqueous medium.

As regards gelled electrolytes, they are liquid electrolytes, for example as described previously, trapped in a "host" polymer. The solvent(s) of the liquid electrolyte must have affinity for the host polymer that is neither too strong (dissolution of the polymer) nor too weak (exudation). The host polymer must allow maximum incorporation of liquid while at the same time conserving mechanical properties to ensure physical separation between the two electrodes.

Finally, to satisfy safety problems associated with the presence of the solvent, it has been proposed to use solid polymer electrolytes. These polymers included in the composition of the electrolyte must have good ion-conducting properties so as to be able to be used satisfactorily in electrochemical storage and generator systems.

It is known practice, for example, to use, as polymer electrolytes not requiring the use of a separator, poly(oxyethylenes) POE in which is dissolved an alkali metal or alkaline-earth metal salt (depending on the chemistry of the electrodes). However, these electrolytes have limited performance qualities in terms of ion conductivity associated with the "assisted" cation transport mechanism, and require a high working temperature (60° C. to 80° C.). The polymers are thus conductors in a gelled physical state.

Mention may also be made, as polymer electrolyte, of the electrolytic membrane of electrochemical generator systems such as proton-exchange-membrane fuel cells, conventionally constituted of a polymer with a fluorocarbon main chain bearing side groups comprising sulfonic acid functions, such as Nafion®. At the present time, the use of polymers of this type for proton conduction requires, however, control of the degree of hydration of the membrane to obtain the desired performance. This type of polymer is a semicrystalline polymer, of which only the amorphous part has conduction properties, the crystalline part imparting the mechanical properties required for its correct functioning in a whole system.

Various studies were conducted for the purpose of increasing the ion-conducting performance of polymer electrolytes.

For example, international patent application WO 00/05774 describes block copolymers with micro-phase separation, constituted of a first ion-conducting block, for example of polyethylene oxide, and of a second block, which is non-conducting and immiscible with the first block to ensure micro-phase separation, for example of polyalkyl acrylate or polydimethylsiloxane type. These polymer electrolytes do not require the addition of an additional salt since an anion (for example carboxylate, sulfonate or phosphate) is immobilized on the polymer.

A mixture of a polystyrene bearing sulfonyl(trifluoromethylsulfonyl)imide and POE groups to make an electrolyte membrane has also been proposed (Meziane et al. Electrochimica Acta, 2011, 57, 14-19). However, these polymer electrolytes have insufficient ion conductivities, of the order of $9.5 \times 10^{-6}$ S/cm at 70° C. Furthermore, for the majority of the current fields of application, it is not possible to use working temperatures above 70° C.

Finally, mention may also be made of FR 2 979 630, which proposes a solid electrolyte of a BA-type diblock copolymer or a BAB-type triblock copolymer, with A being an unsubstituted polyoxyethylene chain and B an anionic polymer formed from one or more monomers of vinyl type and derivatives, substituted with a sulfonyl(trifluoromethylsulfonyl)imide (TFSI) anion. The maximum conductivity, of the order of $10^{-5}$ S/cm, is obtained at 60° C. with a polymer comprising 78% by mass of POE.

For obvious reasons, improving the performance of electrolytes is an ongoing objective.

There thus remains a need for an electrolyte which has high ion conductivity and which preferably has a transport number that is as close as possible to unity.

The need also remains for an electrolyte which has improved electrochemical stability, especially over a broadened temperature range.

The present invention is specifically directed toward proposing novel ion-conducting, cation-conducting or proton-conducting electrolytes, which have improved ion conductivity and electrochemical stability.

More particularly, the invention relates, according to a first of its aspects, to a thermotropic ionic liquid crystal molecule comprising:

a "rigid" part, constituted of a polycyclic group Ar formed from 2 to 6 rings, at least one of which is aromatic, said rings being, independently of each other, 4- to 6-membered, said polycyclic group possibly including up to 18 heteroatoms, chosen in particular from S, N and O;

a "flexible" part, formed from one or more linear or branched, saturated or unsaturated, fluorinated or nonfluorinated aliphatic chains, said chain(s) being optionally interrupted with one or more heteroatoms, with one or more metalloids and/or with one or more aromatic or nonaromatic, 4- to 6-membered (hetero)cycles, and optionally substituted with one or more groups chosen from the group constituted by hydroxyl, $—NH_2$ and oxo groups;

said flexible part being covalently bonded, directly or via a spacer, to said rigid part; and one or more ionic groups $-A^{x-}C^{x+}$, $-A^{x-}$ being an anionic group covalently bonded to said rigid part, with x being an integer equal to 1 or 2, $-A^{x-}$ being chosen from the group constituted of sulfonate anions, sulfonylimide of formula $—SO_2—N^-—SO_2C_yF_{2y+1}$ with y being an integer ranging from 0 to 4, borate, borane, phosphate, phosphinate, phosphonate, silicate, carbonate, sulfide, selenate, nitrate and perchlorate; and $C^{x+}$ being a counter-cation of the anionic group $-A^{x-}$, chosen from the group constituted of $H^+$ and alkali metal and alkaline-earth metal cations.

A thermotropic liquid crystal is defined by three successive types of states, which it has depending on the temperature.

Below its melting point, it is in a crystalline state (or crystalline phase). Then, above its melting point, it passes into a mesomorphic state constituted of a mesophase or of a succession of mesophases. Finally, above its clarification temperature, it passes into an isotropic state (or amorphous phase).

The term "melting point" means the temperature at which a thermotropic liquid crystal passes from a crystalline state to a mesomorphic state.

The term "clarification temperature" means the temperature at which a thermotropic liquid-crystal leaves its mesophase or its last mesophase of a succession of mesophases to enter an isotropic (or liquid) state.

The term "mesomorphic state" means the state in which a thermotropic liquid crystal is found when it is brought to a temperature above its melting point and below its classification temperature.

The term "ionic liquid crystal" means a liquid crystal bearing at least one ionic group, known as $-A^{x-}C^{x+}$.

As illustrated in the examples that follow, the inventors have shown that when the thermotropic ionic liquid crystal molecules of the invention are in a mesomorphic state, they have ion (cation or anion) or proton conductivity.

The temperature range within which a thermotropic liquid crystal molecule is in a mesomorphic state may be determined via a method known to those skilled in the art, for instance DSC (differential scanning calorimetry).

This characterization method also allows the melting point and clarification temperature to be measured.

The nature of the mesophases of a mesomorphic state may be determined by a combination of other characterizations such as PLM (polarized light microscopy), XRD (x-ray diffraction) and/or SAXS (small angle x-ray scattering), the latter technique generally being used as a complement to XRD.

Thus, according to another of its aspects, the invention relates to the use of a thermotropic ionic liquid crystal molecule as defined previously, in a mesomorphic state, as electrolyte in an electrochemical system.

The invention also relates to an electrolyte comprising, or even being formed from, thermotropic ionic liquid crystal molecules as defined previously, in a mesomorphic state.

The molecules according to the invention may be used as electrolytes in numerous electrochemical systems, such as generators, for example lithium batteries, and electrochemical conversion systems, for example proton-exchange-membrane fuel cells (PEMFC).

The use of the molecules according to the invention as electrolytes proves to be advantageous in many respects.

Firstly, since these molecules are ion conductors in a mesomorphic state, they have a substantially broadened working temperature as electrolyte, which may be in the entire temperature range in which the molecules are in a mesomorphic state, which generally corresponds to the temperature range between the melting point and the clarification temperature. The molecules of the invention may also be ion conductors at a temperature beyond their clarification temperature.

An electrochemical system, for example a lithium battery, made with an electrolyte according to the invention may thus function over a wide temperature range, preferably between −60° C. and +300° C. and more preferentially between −20° C. and +200° C.

Moreover, the ion conductivity of an electrolyte according to the invention is based on a "direct" conduction mechanism, by "hopping" of the $C^{x+}$ cations from one anionic group $-A^{x-}$, located on a polycyclic group Ar, to another, and not via an assisted mechanism as is the case, for example, for the polymer electrolytes proposed by Cohen et al. Molecular Transport in Liquids and Glasses, J. Chem. Phys. 31, 1164 (1959). Without wishing to be bound to a particular theory, this mechanism is permitted by the arrangement of the molecules of the invention in a mesomorphic state.

An electrolyte according to the invention thus leads to improved performance in terms of ion, proton or cation conductivity.

Other characteristics, variants and advantages of the molecules and electrolytes according to the invention, the preparation thereof and the use thereof will emerge more clearly on reading the description, examples and figures which will follow, which are given as nonlimiting illustrations of the invention.

In the continuation of the text, the expressions "between . . . and . . . ", "ranging from . . . to . . . " and "varying from . . . to . . . " are equivalent and are intended to mean that the limits are included, unless otherwise mentioned.

Unless otherwise indicated, the expression "comprising a(n)" should be understood as meaning "comprising at least one".

Molecules of the Invention

As mentioned previously, the thermotropic ionic liquid crystal molecules according to the invention comprise:

a "rigid" part, constituted of a polycyclic group Ar formed from 2 to 6 rings, at least one of which is aromatic, said rings being, independently of each other, 4- to 6-membered, said polycyclic group possibly including up to 18 heteroatoms, chosen in particular from S, N and O;

a "flexible" part, formed from one or more linear or branched, saturated or unsaturated, fluorinated or non-fluorinated aliphatic chains, said chain(s) being optionally interrupted with one or more heteroatoms, with one or more metalloids and/or with one or more aromatic or nonaromatic, 4- to 6-membered (hetero)cycles, and optionally substituted with one or more groups chosen from the group constituted by hydroxyl, —$NH_2$ and oxo groups;

said flexible part being covalently bonded, directly or via a spacer, to said rigid part, and one or more ionic groups -$A^{x-}C^{x+}$, -$A^{x-}$ being an anionic group covalently bonded to said rigid part, with x being an integer equal to 1 or 2, -$A^{x-}$ being chosen from the group constituted of sulfonate anions, sulfonylimide of the type —$SO_2$—$N^-$—$SO_2C_yF_{2y+1}$ with y being an integer ranging from (to 4, borate, borane, phosphate, phosphinate, phosphonate, silicate, carbonate, sulfide, selenate, nitrate and perchlorate; and $C^{x+}$ being a counter-cation of the anionic group -$A^{x-}$, chosen from the group constituted of $H^+$ and alkali metal and alkaline-earth metal cations.

In the context of the invention, the following definitions apply:

"alkyl": a saturated, linear or branched aliphatic group; for example, a $C_{1-4}$alkyl group represents a linear or branched carbon-based chain of 1 to 4 carbon atoms, and more particularly a methyl, ethyl, propyl, isopropyl, butyl, isobutyl or tert-butyl;

"4- to 6-membered aromatic or nonaromatic (hetero) cycle": an unsaturated, partially saturated or saturated, 4-, 5- or 6-membered cyclic group, optionally comprising one or more heteroatoms, chosen in particular from the group constituted of oxygen, sulfur and nitrogen. An aromatic ring may especially be benzene;

"polycyclic group": a group containing two or more nuclei (rings), condensed (ortho-condensed or ortho- and peri-condensed) on each other, i.e. having, in pairs, at least two carbons in common.

In particular, a polycyclic group according to the invention is formed from two to six rings, the rings being, independently of each other, 4- to 6-membered.

The polycyclic group may include one or more heteroatoms. It is then referred to as a "polyheterocyclic group".

"alkali metals": the chemical elements in the first column of the Periodic Table of the Elements, and more particularly chosen from the group constituted of lithium, sodium, potassium, rubidium and cesium. Preferably, the alkali metal is lithium, sodium or potassium, and more preferentially lithium;

"alkaline-earth metals": the chemical elements in the second column of the Periodic Table of the Elements, and more particularly chosen from the group constituted of beryllium, magnesium, calcium, strontium, barium and radium. Preferably, the alkaline-earth metal is magnesium or potassium "metalloids": the following chemical elements: boron, silicon, germanium, arsenic, antimony, tellurium and astatine. Preferably, the metalloid is boron or silicon;

"spacer": an atom or a group of atoms with a valency at least equal to 2, covalently connecting the rigid part and the flexible part. Preferably, the spacer connects the rigid part to at least two, preferably two, aliphatic chains of the flexible part. Preferably, the spacer is a divalent or trivalent atom, advantageously a trivalent atom. Suitable spacers that may be mentioned include nitrogen, oxygen, phosphorus and sulfur atoms.

Rigid Part

Ar is a 4- to 6-membered polycyclic group comprising from 2 to 6 rings, preferably from 2 to 4 rings, at least one of the rings being aromatic and preferably representing a benzene ring.

According to one variant, Ar is an aromatic polycyclic group formed from 2 to 6 6-membered fused aromatic rings, preferably from 2 to 6 fused benzene rings, advantageously from 2 to 4 fused benzene rings.

More particularly, Ar may have one of the following polycyclic backbones:

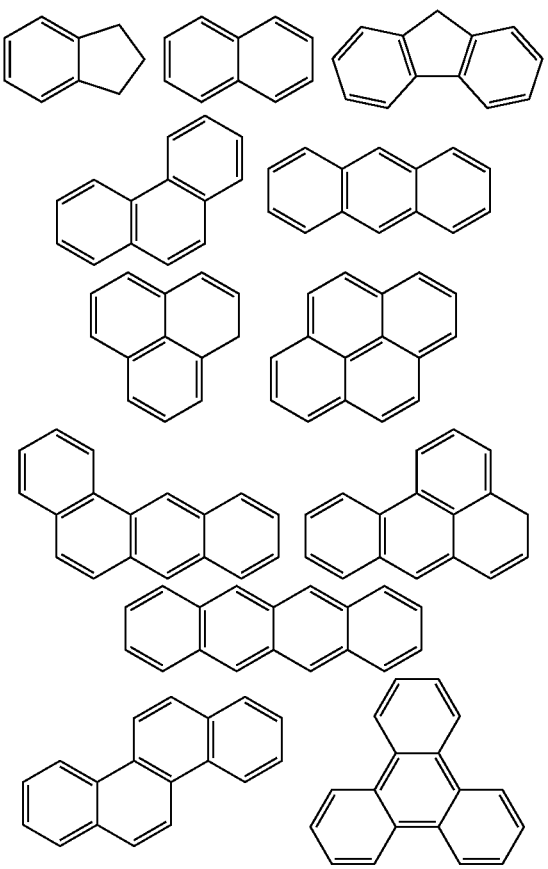

It is understood that the group Ar may be a polyheterocyclic group having one of the backbones presented above in which one or more carbon atoms are replaced with one or more heteroatoms, chosen especially from the group constituted of S, N and O.

According to a particular embodiment, Ar is an aromatic bicyclic group, in particular with a naphthalene aromatic backbone.

Preferably, Ar is a naphthalene group.

Flexible Part

Preferably, the aliphatic chain(s) of the flexible part comprise from 4 to 18 carbon atoms.

Preferably, the aliphatic chain(s) of the flexible part are substituted with at least one, or even one, hydroxyl group.

According to one embodiment, the flexible part is formed from:

a single branched aliphatic chain, containing a linear sequence of at least 6 covalent bonds; or at least two linear or branched aliphatic chains, each of the chains containing a linear sequence of at least 6 covalent bonds.

According to a particular embodiment, each of the aliphatic chains is formed from a single chain segment or from a linear sequence of at least two chain segments, in particular from two or three chain segments of different chemical nature.

Preferably, each of the aliphatic chains represents a linear alkyl chain comprising from 6 to 18 carbon atoms, preferably from 6 to 12 carbon atoms, which is optionally fluorinated, optionally substituted with at least one, or even one, hydroxyl group, and optionally interrupted with one or more oxygen atoms.

According to one variant, said aliphatic chain(s) forming said flexible part are covalently bonded directly to one or more carbon atoms or heteroatoms of the group Ar forming the rigid part.

In this variant, a heteroatom preferably denotes a nitrogen atom.

According to another variant, said aliphatic chain(s) forming said flexible part are covalently bonded via a spacer to one or more carbon atoms or heteroatoms of the group Ar forming the rigid part.

In this variant, a heteroatom preferably denotes a nitrogen atom.

When the flexible part is formed from at least two aliphatic chains, they are preferably covalently bonded via a single spacer to the same carbon atom of the group Ar forming the rigid part.

When the flexible part is formed from two aliphatic chains, they are preferably covalently bonded via a single trivalent spacer to the same carbon atom of the group Ar forming the rigid part.

According to this variant, said aliphatic chain(s) forming said flexible part are preferably covalently bonded to a carbon atom of the group Ar via an atom of valency greater than or equal to 2, in particular via a nitrogen atom.

Said atom of valency greater than or equal to 2, in particular said nitrogen atom, acts as a spacer covalently connecting said aliphatic chain(s) forming said flexible part and the group Ar forming the rigid part.

When the flexible part is formed from at least two aliphatic chains, they are preferably covalently bonded to the same carbon atom of the group Ar forming the rigid part via a single atom of valency greater than or equal to 2.

When the flexible part is formed from two aliphatic chains, they are preferably covalently bonded to the same carbon atom of the group Ar forming the rigid part via a single atom of valency equal to 2, in particular via a single nitrogen atom.

According to a particular embodiment, the flexible part is formed from two linear alkyl chains, which may be identical or different, preferably identical, comprising from 4 to 18 carbon atoms, preferably from 6 to 16 carbon atoms, optionally substituted with one or more hydroxyl groups, optionally interrupted with one or more oxygen atoms, said chains being bonded to a carbon atom of the group Ar via a nitrogen atom, preferably to the same carbon atom of the group Ar via a single nitrogen atom.

According to a preferred embodiment, the flexible part is formed from two linear alkyl chains, comprising from 6 to 16 carbon atoms, each being substituted with a hydroxyl group and optionally interrupted with an oxygen atom, said chains being bonded to a carbon atom of the group Ar via a nitrogen atom, preferably to the same carbon atom of the group Ar via a single nitrogen atom.

Ionic Group

In the thermotropic ionic liquid crystal molecules of the invention, the anionic group $-A^{x-}$ may be chosen more particularly from the group constituted of sulfonate anions (of formula $-SO_3^-$) and anions of formula $-SO_2-N^--SO_2-C_yF_{2y+1}$ with y ranging from 0 to 4, preferably equal to 1.

Preferably, $-A^{x-}$ is a sulfonate anion.

Preferably, $-A^{x-}$ is an anion of formula $-SO_2-N^--SO_2-CF_3$.

According to one implementation variant of the invention, $C^{x+}$ represents a proton $H^+$.

According to this variant, the group $-A^{x-}C^{x+}$ preferably represents a $-SO_3^-H^+$ group, in which the sulfur atom is covalently bonded to a carbon atom or a heteroatom of the rigid part.

As detailed in the continuation of the text, such molecules may be advantageously used as electrolyte in a proton-exchange-membrane fuel cell (PEMFC) or a low-temperature electrolyzer.

According to another implementation variant of the invention, $C^{x+}$ represents the $Li^+$ cation.

According to this variant, the group $-A^{x-}C^{x+}$ preferably represents a $-SO_3^-Li^+$ group, in which the sulfur atom is covalently bonded to a carbon atom or a heteroatom of the rigid part.

As detailed in the continuation of the text, such molecules may be advantageously used as electrolyte in a lithium battery.

According to a particular embodiment, the molecules according to the invention have the following structure:

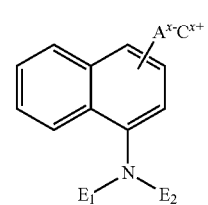

(I)

in which $-A^{x-}$ and $C^{x+}$ are as defined above, and $E_1$ and $E_2$ represent identical or different aliphatic chains, as defined above.

Preferably, $E_1$ and $E_2$ represent identical aliphatic chains.

Preferably, the general formula (I) corresponds to one of the two sub-formulae below:

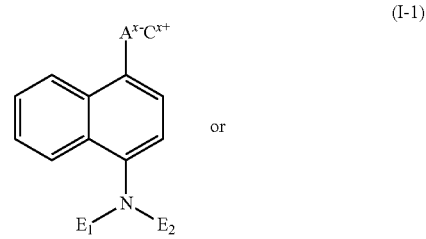

(I-1)

or

-continued

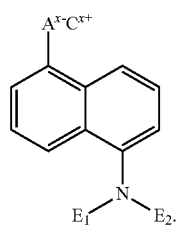

(I-2)

in which -A$^{x-}$ and C$^{x+}$ are as defined above, and E$_1$ and E$_2$ represent identical or different aliphatic chains, as defined above.

According to a particular embodiment, the chains E$_1$ and E$_2$ represent identical or different linear alkyl chains, comprising from 4 to 18 carbon atoms, preferably from 6 to 16 carbon atoms, which are optionally fluorinated, optionally substituted with one or more hydroxyl groups, optionally interrupted with one or more oxygen atoms.

According to a preferred embodiment, the chains E$_1$ and E$_2$ represent identical or different linear alkyl chains, comprising from 6 to 16 carbon atoms, each being substituted with a hydroxyl group, optionally fluorinated, and optionally interrupted with an oxygen atom.

The chains E$_1$ and E$_2$ preferably correspond to the general formula —CH$_2$—CHOH—R, in which R is an optionally fluorinated C$_4$-C$_{18}$ alkyl group, optionally interrupted with one or more oxygen atoms.

Preferably, the thermotropic ionic liquid crystal molecules in accordance with the invention are not polymers.

Advantageously, the thermotropic ionic liquid crystal molecules in accordance with the invention have a molecular mass of less than or equal to 1500 g/mol, preferentially less than 1000 g/mol.

The thermotropic ionic liquid crystal molecules in accordance with the invention are particularly efficient as electrolyte when the flexible part/rigid part mass ratio (excluding the ionic group(s)) is from 1/1 to 100/1, preferentially from 1/1 to 50/1 and advantageously from 1/1 to 10/1.

A subject of the present invention is especially the following thermotropic ionic liquid crystal molecules, which are particularly suitable for use as electrolyte:

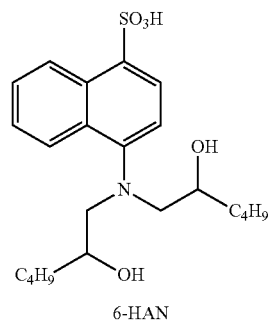

6-HAN

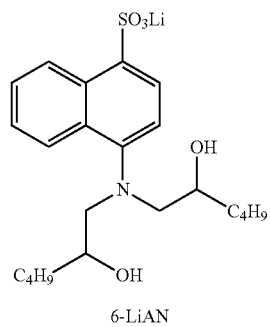

6-LiAN

-continued

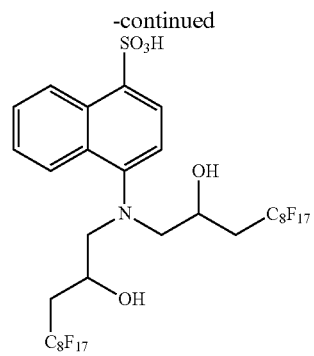

8F-HAN

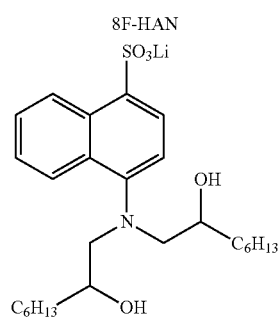

8-LiAN

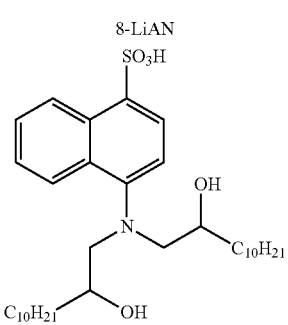

12-HAN

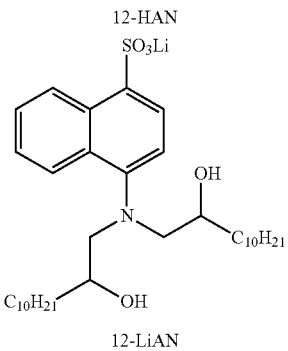

12-LiAN

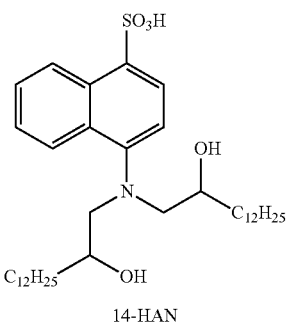

14-HAN

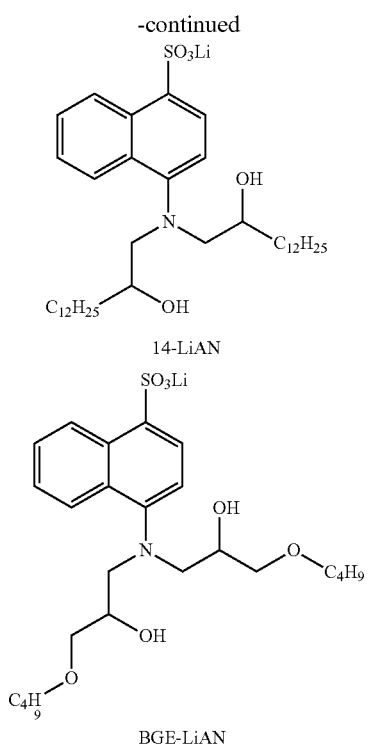

14-LiAN

BGE-LiAN

16-LiAN

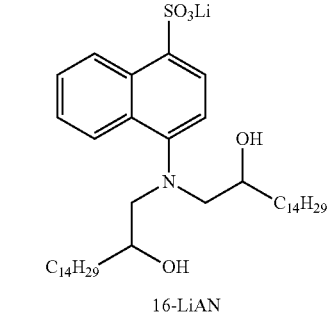

12-LiAN'

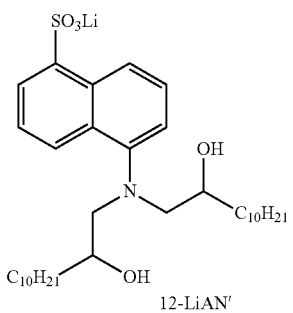

16-LiAN'

Preparation of the Compounds of the Invention

The molecules according to the invention may be prepared using nucleophilic addition or substitution methods known to those skilled in the art, as detailed below.

The molecules of the invention may be prepared by placing, under conditions suitable for their interaction via a nucleophilic addition or substitution reaction known to those skilled in the art, a precursor of the rigid part in contact with a precursor of the flexible part.

The precursor of the rigid part advantageously bears the ionic group(s) $-A^{x-}C^{x+}$ or alternatively bears one or more precursors of said ionic groups.

According to one embodiment, the precursor of the rigid part bears a nucleophilic group, for example of amine, hydroxyl or sulfide type, and the precursor of the flexible part bears an electrophilic group of epoxide, halogen, isocyanate, nitrile, thiocarbonyl or carbonyl type.

Alternatively, the precursor of the flexible part bears a nucleophilic group, for example of amine, hydroxyl or sulfide type, and the precursor of the rigid part bears an electrophilic group of epoxide, halogen, isocyanate, nitrile, thiocarbonyl or carbonyl type.

As illustrations of the methods that a person skilled in the art can use to arrive at the molecules of the invention, a method for preparing the molecules of the invention of formula (I) is described below and also in the examples that follow.

The molecules of the invention of formula (I) may be prepared according to a process comprising at least the placing of a compound of formula (I) below:

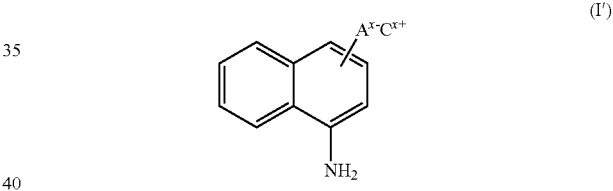

(I')

in contact with a precursor of the chain $E_1$ and a precursor of the chain $E_2$, said precursors being optionally identical when $E_1$ and $E_2$ are identical, under conditions suitable for their interaction via a nucleophilic addition reaction.

This reaction is preferably performed in a polar aprotic solvent, such as dimethylformamide.

This reaction is preferably performed by heating the reaction mixture composed of the compound of formula (I'), the precursors and said solvent to a temperature of from 80° C. to 120° C.

This reaction is preferably performed in the presence of at least one equivalent of the precursor of the chain $E_1$ and of at least one equivalent of the precursor of the chain $E_2$, relative to the compound of formula (I').

The precursors of the chains $E_1$ and $E_2$ advantageously bear an electrophilic group of epoxide, halogen, isocyanate, nitrile, thiocarbonyl or carbonyl type, preferably an epoxide group.

The molecules of the invention of formula (I) in which $E_1$ and $E_2$ are identical may be obtained via a nucleophilic addition reaction between a compound of formula (I') and a precursor of the chains $E_1$ and $E_2$ bearing an electrophilic group, for instance an epoxide group. This reaction is preferably performed in the presence of at least two equivalents of the precursor of the chains $E_1$ and $E_2$ relative to the compound of formula (I').

Needless to say, it falls to a person skilled in the art to adjust the synthetic conditions to obtain the molecules according to the invention.

Use as Electrolyte

The thermotropic ionic liquid crystal molecules according to the invention may be advantageously used, in a mesomorphic state, as electrolyte in an electrochemical system.

As mentioned above, a mesomorphic state denotes the mesophase or the succession of mesophases in which the thermotropic ionic liquid crystal molecules according to the invention are found as a function of their temperature, lying between the melting point and the clarification temperature.

The electrolyte formed from such molecules is advantageously used in combination with a porous separator onto which said electrolyte is impregnated, said separator providing a physical separation between the two electrodes of the electrochemical system.

The separator that may be used is any porous separator conventionally used in an electrochemical system, for instance a porous separator of a lithium battery or an ion-exchange membrane of a fuel cell. A person skilled in the art is capable of choosing a separator that is suitable for the implementation of the electrolyte.

The thermotropic ionic liquid crystal molecules according to the invention in which $C^{x+}$ represents an $Li^+$ cation may advantageously be used, in a mesomorphic state, as electrolyte in a lithium battery.

The thermotropic ionic liquid crystal molecules according to the invention in which $C^{x+}$ represents $H^+$ may advantageously be used, in a mesomorphic state, as electrolyte in a proton-exchange-membrane fuel cell or a low-temperature electrolyzer.

Electrolyte

As mentioned previously, the thermotropic ionic liquid crystal molecules according to the invention are ion, proton or cation conductors, in their mesomorphic state.

The present invention relates to an electrolyte comprising, or even being formed from, thermotropic ionic liquid crystal molecules as defined above, in a mesomorphic state.

In the electrolyte of the invention, the thermotropic ionic liquid crystal molecules are preferably used at a temperature from 80° C. to 220° C., generally from 100° C. to 200° C., preferentially from 130° C. to 170° C., for example about 150° C.

Preferably, the liquid electrolyte of the invention has a viscosity of greater than or equal to 10 mPa·s, preferably from 100 mPa·s to 100 Pas, at a temperature of between −60° C. and 300° C.

The expression "at a temperature between −60° C. and 300° C." means that the liquid electrolyte of the invention has a viscosity as defined above at at least one temperature located within this range. This does not necessarily mean that the liquid electrolyte of the invention has a viscosity as defined above at any temperature located within this range.

The viscosity may be measured by extrapolation to zero shear on the curve of viscosity as a function of the shear gradient at a given temperature, measured on a cone/plate or plate/plate viscometer/rheometer.

This condition on the viscosity of the liquid electrolyte ensures good impregnation thereof in the separator of the electrochemical system.

The electrolyte according to the invention has good ion conductivity properties.

Preferably, the electrolyte of the invention has an ion conductivity at 20° C. of greater than or equal to $10^{-9}$ S/cm, in particular between $10^{-7}$ S/cm and $10^{-5}$ S/cm and an ion conductivity at 200° C. of greater than or equal to $10^{-3}$ S/cm.

The ion conductivity may be measured by voltage-dependent or current-dependent electrochemical impedance spectroscopy, according to a method known to those skilled in the art.

Electrochemical System

The electrolyte according to the invention may be used in an electrochemical system, for example for a lithium battery.

The present invention thus relates, according to yet another of its aspects, to an electrochemical system comprising an electrolyte according to the invention.

In the electrochemical system of the invention, the electrolyte is preferably impregnated on a porous separator as described previously.

The electrochemical system may be an electrochemical storage, converter or generator system.

It may more particularly be a fuel cell, for example a proton-exchange-membrane fuel cell (PEMFC); a primary or secondary battery, for example a lithium, sodium, magnesium, potassium or calcium battery; a lithium-air or lithium-sulfur accumulator.

According to a particular embodiment, the electrolyte is used in a battery, in particular a lithium battery.

The present invention also relates, according to yet another of its aspects, to a porous separator impregnated with an electrolyte according to the invention.

Such a porous separator is particularly suitable for use in an electrochemical system as described above.

The invention will now be described by means of the examples and figures that follow, which are obviously given as nonlimiting illustrations of the invention.

FIG. 1: Calorimetric analysis of the product 12-HAN by DSC under argon and with a heating rate of 10 K/min.

Figure 2:
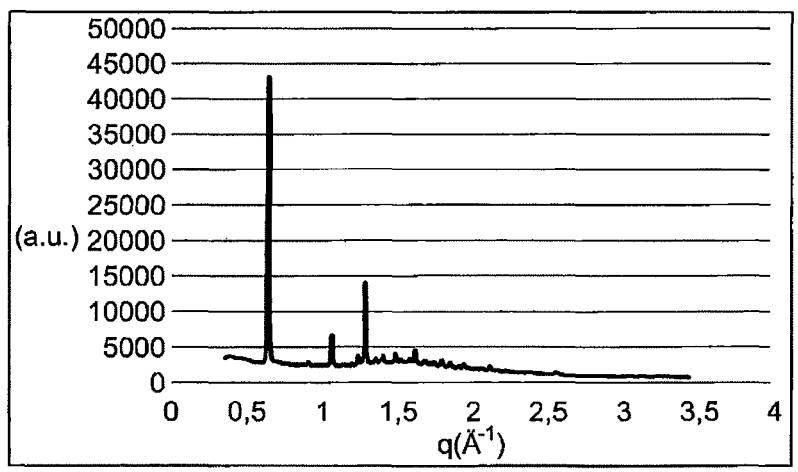

FIG. 2: Analysis of the product 12-HAN by XRD.

Figure 3:
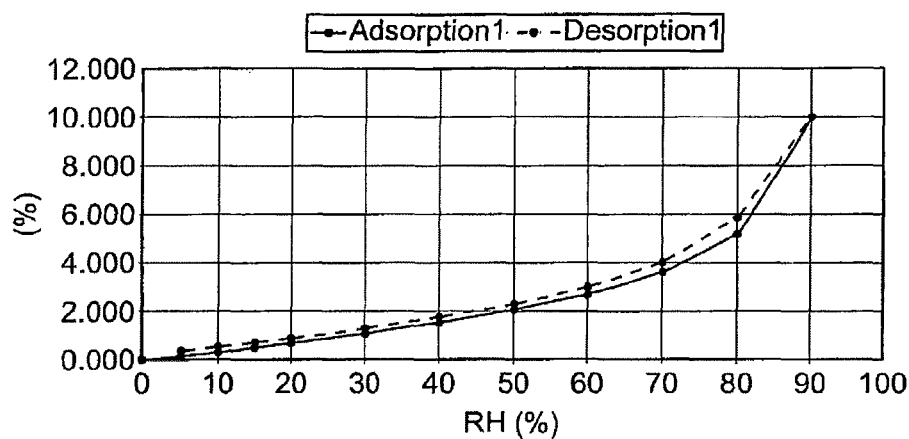

FIG. 3: Isotherms of sorption/desorption of water at 25° C. for the product 12-HAN.

Figure 4:
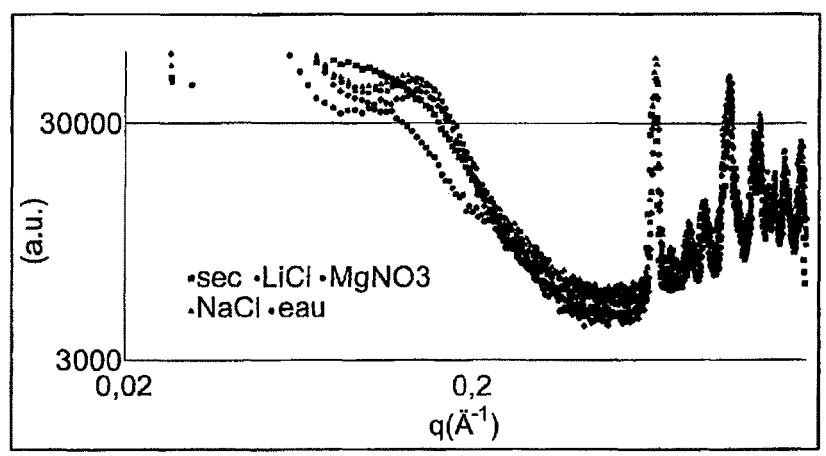

FIG. 4: Analysis of the product 12-HAN by SAXS, as a function of its degree of hydration.

Figure 5:
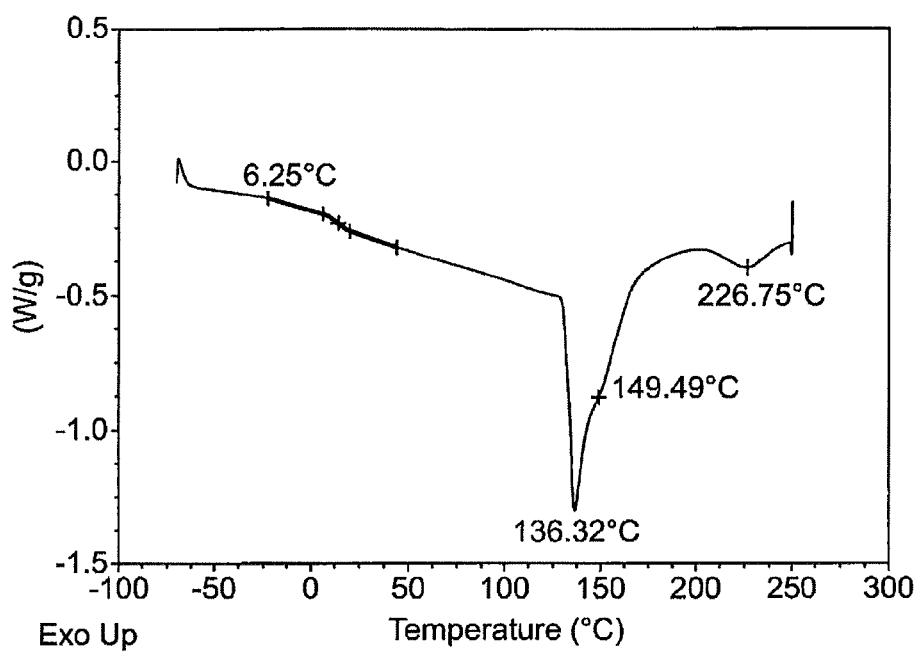

FIG. 5: Calorimetric analysis of the product 12-LiAN by DSC under argon and with a heating rate of 10 K/min.

Figure 6:
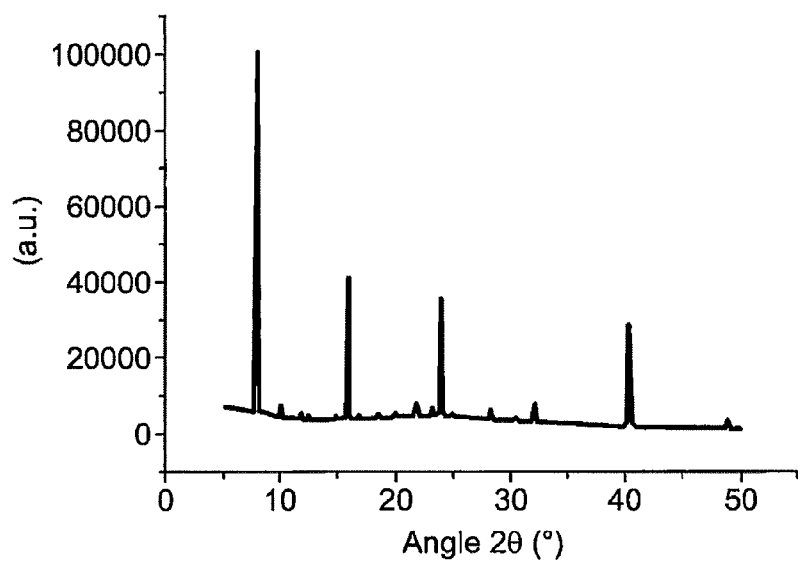

FIG. 6: Analysis of the product 12-LiAN by XRD.

Figure 7:
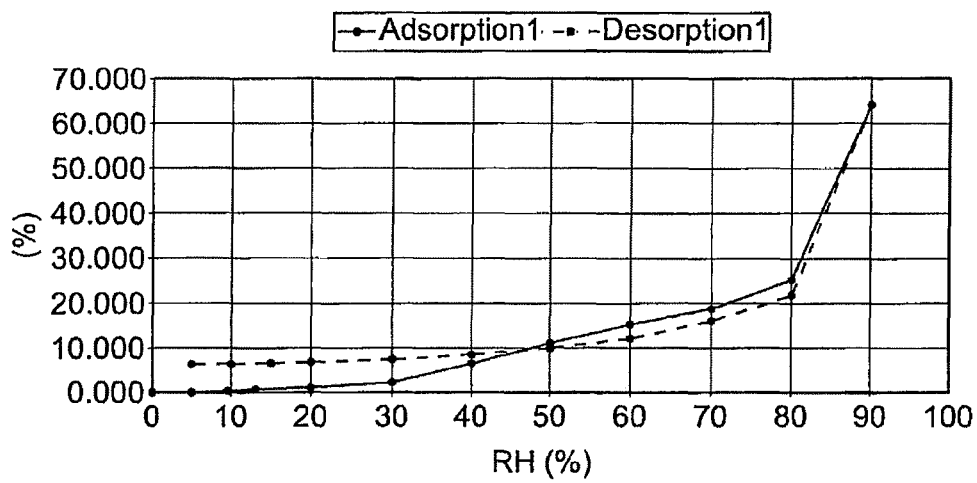

FIG. 7: Isotherms of sorption/desorption of water at 25° C. for the product 12-LiAN.

Figure 8:
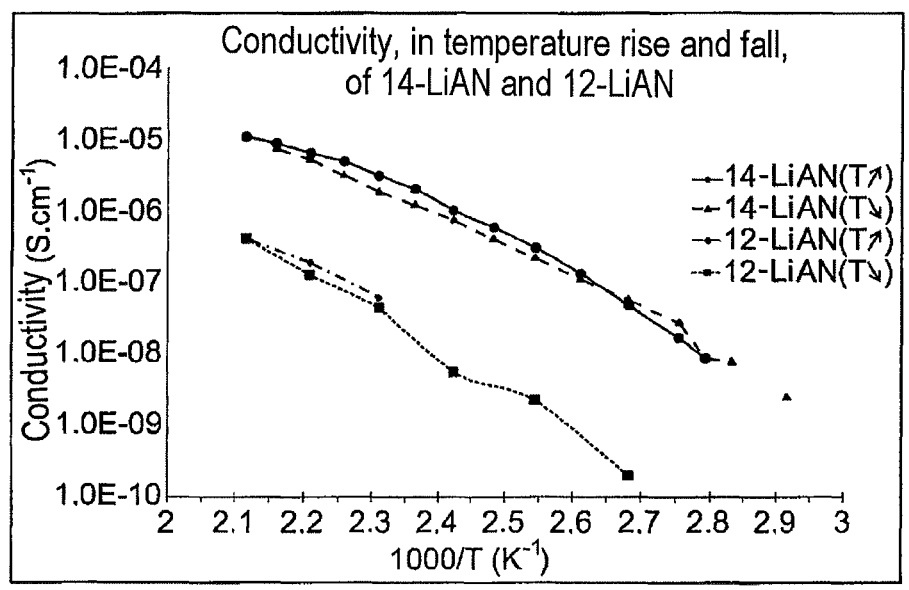

FIG. 8: Ion conductivity analysis, in temperature rise and fall, of the products 12-LiAN and 14-LiAN.

Figure 9:
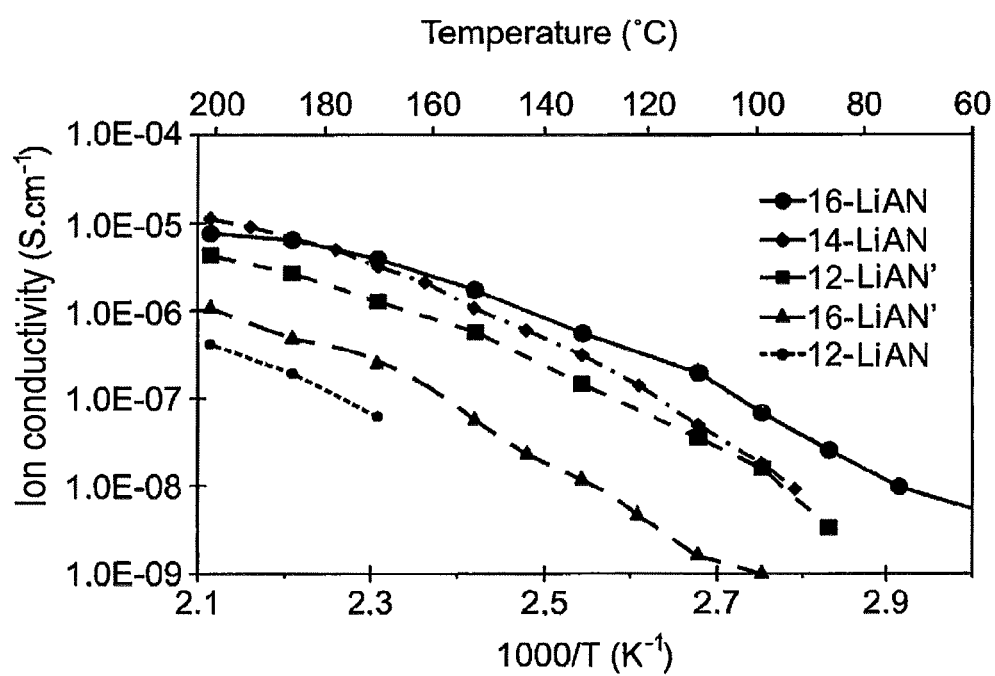

FIG. 9: Ion conductivity analysis, in temperature rise and fall, of the products 12-LiAN, 14-LiAN, 16-LiAN, 12-LiAN' and 16-LiAN'.

EXAMPLES

Preparation of Synthetic Intermediates

Preparation of Lithium 4-amino-1-naphthalenesulfonate (LiAN)

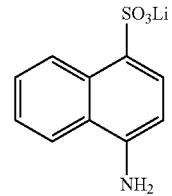

1.340 g of 4-amino-1-naphthalenesulfonic acid (HAN) and 0.210 g of lithium hydroxide monohydrate (LiOH.H$_2$O) were placed in 20 mL of distilled water. The reaction medium was stirred overnight at room temperature. The excess HAN was removed by filtration. The filtrate was then concentrated by evaporating off the solvent under reduced pressure. After washing twice with ethanol, a pink powder (LiAN) was obtained.

$^1$H NMR (400 MHz; DMSO-d6; 300 K): δ ppm 7.89 (dd, 1H); 7.18 (dd, 1H); 6.83 (d, 1H); 6.52 (m, 2H); 5.68 (d, 1H); 4.96 (s, 2H).

$^{13}$C NMR (400 MHz; DMSO-d6; 300 K): δ ppm 146.11; 132.34; 130.61; 128.10; 126.45; 125.33; 123.56; 122.94; 122.26; 105.17.

Preparation of Lithium
5-amino-1-naphthalenesulfonate (LiAN')

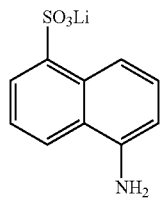

24.441 g of 4-amino-1-naphthalenesulfonic acid (HAN) and 4.282 g of lithium hydroxide monohydrate (LiOH.H$_2$O) were placed in 500 mL of distilled water. The reaction medium was stirred overnight at room temperature. The excess HAN was removed by filtration. The filtrate was then concentrated by evaporating off the solvent under reduced pressure. After washing twice with ethanol, a pink powder (LiAN') was obtained.

Example 1—Preparation of a Liquid Crystal
12-HAN in Accordance with the Invention

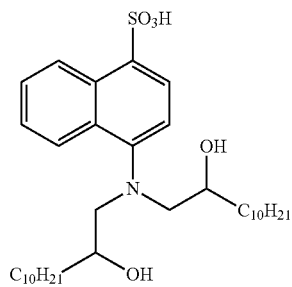

2.0 g (8.96 mmol) of 4-amino-1-naphthalenesulfonic acid (HAN) and 3.29 g (17.9 mmol) of 1,2-epoxydodecane (i.e. 2 equivalents of epoxide per 1 of amine) in 10 mL of dimethylformamide DMF were placed in a 50 mL round-bottomed flask mounted on a reflux assembly equipped with a condenser and a magnetic bar, and also an oil bath on a hotplate. The reaction mixture was stirred and heated at a temperature of 80° C. at the start of the reaction and then raised to 100° C. for 2 days until a brown two-phase mixture was obtained. The reaction products were precipitated from a large volume of diethyl ether and then filtered off on a Büchner funnel. The solid phase was then dissolved in methanol, this methanol being removed on a rotary evaporator.

The product obtained (12-HAN) was dried under reduced pressure and a brown paste was obtained.

Characterization of the Liquid Crystal 12-HAN

The product 12-HAN was characterized by DSC under argon and with a heating rate of 10 K/min. The results of the calorimetric analysis are shown in FIG. 1.

The DSC spectrum shows the phase transition at −38° C. (corresponding to the melting point) and an endothermic peak at 193° C. (corresponding to the clarification temperature).

The liquid crystal 12-HAN was observed by PLM. The liquid crystal is placed between two hydrophilic glass plates (thickness of the deposit: 3-5 μm), slid inside a hotplate and under a controlled atmosphere (nitrogen), which is itself mounted between the polarizer and the analyzer of the microscope.

The PLM image obtained after shear under the glass plates at 185° C. shows the appearance of very small birefringent zones representative of the observation of mesomorphic phase defects.

A deposit of 12-HAN powder was produced on a glass support for XRD analysis.

The x-ray diffractogram, shown in FIG. 2, shows that the liquid crystal 12-HAN has a hexagonal lamellar phase with different peaks in ratios $\sqrt{3}$, $\sqrt{4}$, $\sqrt{7}$.

Evaluation of the hygroscopicity of the liquid crystal 12-HAN was performed by conducting the study of the isotherm of sorption/desorption of water in the vapor phase in accordance with the method described below.

The sorption balance was equipped with an electronic microbalance and a dew point analyzer. The liquid crystal 12-HAN was predried at 60° C. in an oven under vacuum. The liquid crystal 12-HAN was then dried again in the balance at 60° C. with a ramp of 5° C./min until an equilibrium of 0.0010% mass uptake over 10 minutes was achieved. If these conditions were not met, the liquid crystal was dried up to a maximum time of 600 minutes. The end condition used was 0.005% mass change for a time of 20 minutes. During the sorption/desorption cycle, the maximum time required to reach equilibrium was 1000 minutes.

FIG. 3 shows the isotherms of sorption/desorption of water at 25° C., showing that the liquid crystal 12-HAN is hydrophilic.

The liquid crystal 12-HAN was also characterized by SAXS, as a function of its degree of hydration.

The degree of hydration of the samples was controlled using a controlled atmosphere. The liquid crystal 12-HAN was dried in an oven at 60° C. for one week under vacuum to obtain a dry sample. The liquid crystal 12-HAN was then analyzed by SAXS and the relative humidity of the room was measured using a hygrometer. The sample was then left to equilibrate for 1, 3 and 6 hours. To obtain a hydrated sample in an atmosphere containing 100% humidity, it was placed in a crucible to avoid direct contact with water. This same crucible was placed in a hermetic system filled with water. A water-saturated system in which the sample can become hydrated was then obtained.

A shift of the "ionomer peak" with hydration of the liquid crystal 12-HAN is observed (FIG. 4).

The "ionomer peak" is the signature of phase separation between the hydrophilic and hydrophobic domain at the nanometric scale. Its position (q) directly reflects the state of nanometric swelling or the correlation distance between the hydrophilic (or hydrophobic) domains (d=2π/q). The more this peak is shifted toward the small values of "q" (the more d increases), the greater the amount of water in the product.

Example 2—Preparation of a Liquid Crystal 12-LiAN in Accordance with the Invention

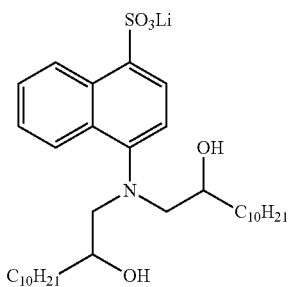

This product was synthesized via a protocol similar to that described in example 1, using 1.050 g of LiAN (4.73 mmol) instead of HAN with 1.741 g (9.46 mmol) of 1,2-epoxydodecane in 10 mL of DMF. The reaction is maintained at 70° C. for 3 days. A yellow-brown powder (12-LiAN) is obtained.

Characterization of the Liquid Crystal 12-LiAN

The results of the DSC analysis under argon and with a heating rate of 10 K/min are shown in FIG. 5. The DSC spectrum shows the phase transition at 6.25° C. (corresponding to the melting point) and an endothermic peak at 226° C. (corresponding to the clarification temperature).

A deposit of 12-LiAN powder was produced on a glass support for X-ray diffraction analysis.

The XRD analysis shown in FIG. 6 shows that the compound 12-LiAN has a lamellar phase with different peaks in ratios 2, 3, 4, 5.

Evaluation of the hygroscopicity of the liquid crystal 12-LiAN was performed by conducting the study of the sorption/desorption isotherm of water in the vapor phase, according to the protocol detailed in example 1.

FIG. 7 shows the isotherms of sorption/desorption of water at 25° C., showing that the liquid crystal 12-LiAN is hydrophilic.

Example 3—Preparation of the Liquid Crystal 6-HAN in Accordance with the Invention

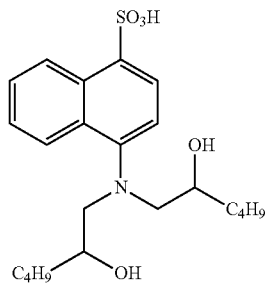

3.101 g (13.47 mmol) of HAN and 3.35 mL (26.94 mmol) of 1,2-epoxyhexane in 15 mL of dimethylformamide DMF were placed in a 50 mL round-bottomed flask mounted on a reflux assembly equipped with a condenser and a magnetic bar, and also an oil bath on a hotplate. The reaction mixture was stirred and heated under argon at a temperature of 100° C. for 120 hours until a homogeneous brown mixture was obtained. The reaction products were precipitated from a large volume of diethyl ether and then filtered off on a Büchner funnel.

The product obtained (6-HAN) was dried under reduced pressure and a brown paste was obtained.

Example 4—Preparation of the Liquid Crystal 6-LiAN in Accordance with the Invention

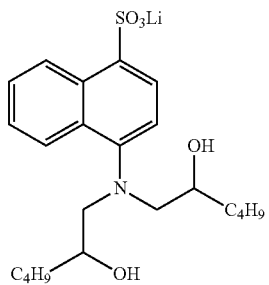

3.122 g (13.62 mmol) of LiAN and 3.39 mL (27.24 mmol) of 1,2-epoxyhexane in 15 mL of dimethylformamide DMF were placed in a 50 mL round-bottomed flask mounted on a reflux assembly equipped with a condenser and a magnetic bar, and also an oil bath on a hotplate. The reaction mixture was stirred and heated under argon at a temperature of 100° C. for 144 hours until a very dark red homogeneous mixture was obtained. The reaction products were precipitated from a large volume of diethyl ether and then filtered off on a Büchner funnel.

The product obtained (6-LiAN) was dried under reduced pressure and a bordeaux-red paste was obtained.

The SAXS temperature observations confirmed the existence of an organized structure, proving that 6-LiAN is a thermotropic ionic liquid crystal.

Example 5—Preparation of the Liquid Crystal 8-LiAN in Accordance with the Invention

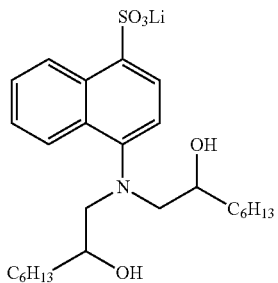

3.03 g (13.19 mmol) of LiAN and 4.21 mL (26.38 mmol) of 1,2-epoxyoctane in 15 mL of dimethylformamide DMF were placed in a 50 mL round-bottomed flask mounted on a reflux assembly equipped with a condenser and a magnetic bar, and also an oil bath on a hotplate. The reaction mixture was stirred and heated under argon at a temperature of 60° C. for 96 hours, then at 65° C. for 144 hours, then at 75° C. for 264 hours and then at 85° C. for 3 weeks until a very dark homogeneous mixture was obtained. The reaction products were precipitated from a large volume of diethyl ether and then filtered off on a Büchner funnel.

The product obtained (8-LiAN) was dried under reduced pressure and a dark red powder was obtained.

Example 6—Preparation of the Liquid Crystal 14-HAN in Accordance with the Invention

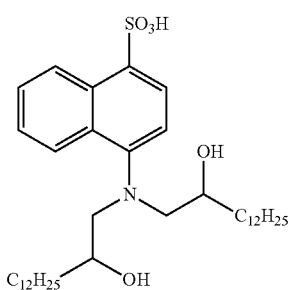

3.136 g (13.62 mmol) of HAN and 8.057 mL (27.25 mmol) of 1,2-epoxytetradecane in 15 mL of dimethylformamide DMF were placed in a 50 mL round-bottomed flask mounted on a reflux assembly equipped with a condenser and a magnetic bar, and also an oil bath on a hotplate. The reaction mixture was stirred and heated under argon at a temperature of 90° C. for 144 hours until a very dark red homogeneous mixture was obtained. The reaction products were precipitated from a large volume of diethyl ether and then filtered off on a Büchner funnel.

The product obtained (14-HAN) was dried under reduced pressure and an orange-red powder was obtained.

Example 7—Preparation of the Liquid Crystal 14-LiAN in Accordance with the Invention

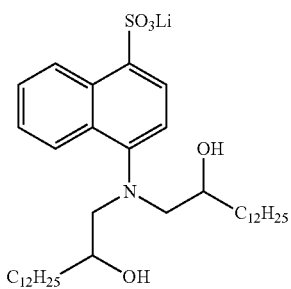

3.008 g (13.12 mmol) of LiAN and 7.76 mL (26.25 mmol) of 1,2-epoxytetradecane in 15 mL of dimethylformamide DMF were placed in a 50 mL round-bottomed flask mounted on a reflux assembly equipped with a condenser and a magnetic bar, and also an oil bath on a hotplate. The reaction mixture was stirred and heated under argon at a temperature of 90° C. for 144 hours until a very dark brown homogeneous mixture was obtained. The reaction products were precipitated from a large volume of diethyl ether and then filtered off on a Büchner funnel.

The product obtained (14-LiAN) was dried under reduced pressure and a red powder was obtained.

The observations by DSC, PLM and SAXS confirmed that 14-LiAN is a thermotropic ionic liquid crystal.

The DSC spectrum does not show the phase transition corresponding to the melting point (since it is below the minimum measurement temperature) but shows three endothermic peaks characteristic of three mesomorphic phase changes.

The changes in the SAXS spectra on temperature rise and fall, and also the PLM images, made it possible to identify the three mesomorphic phases: lamellar, lamello-columnar and columnar.

Example 8—Preparation of the Liquid Crystal 16-LiAN in Accordance with the Invention

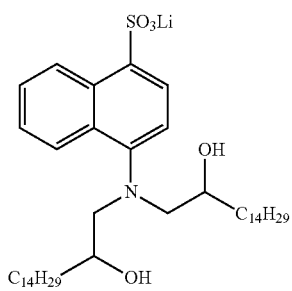

2.991 g (13.12 mmol) of LiAN and 7.380 g (26.10 mmol) of 1,2-epoxyhexadecane in 25 mL of dimethylformamide DMF were placed in a 100 mL round-bottomed flask mounted on a reflux assembly equipped with a condenser and a magnetic bar, and also an oil bath on a hotplate. The reaction mixture was stirred and heated under argon at a temperature of 100° C. for 2 weeks until a very dark brown homogeneous mixture was obtained. The reaction products were precipitated from a large volume of diethyl ether and then filtered off on a Büchner funnel.

The product obtained (16-LiAN) was dried under reduced pressure and a red powder was obtained.

The observations by DSC and SAXS confirmed that 16-LiAN is a thermotropic ionic liquid crystal with two main mesomorphic phases of lamellar type with a mesomorphic phase transition at about 50° C.

Example 9—Preparation of the Liquid Crystal 8F-HAN in Accordance with the Invention

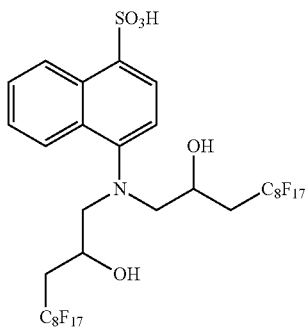

1.00 g of HAN (4.48 mmol) and 4.26 g (8.95 mmol) of 1,2-epoxy-1H,1H,2H,3H,3H-heptadecafluorodecane in 10 mL of DMF were placed in a round-bottomed flask equipped with a condenser and a magnetic bar. The reaction mixture was stirred and heated under argon at 80° C. in air for 2 days until a homogeneous mixture was obtained. The compound was precipitated from diethyl ether and filtered off on a Büchner funnel. The product was dried under reduced pressure, and a stable reddish gel was obtained (8F-HAN).

Example 10—Preparation of the Liquid Crystal BGE-LiAN in Accordance with the Invention

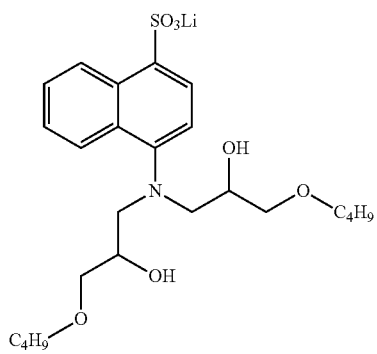

3.034 g (13.24 mmol) of LiAN and 3.99 mL (26.48 mmol) of butyl glycidyl ether were placed in a 25 mL round-bottomed flask mounted on a reflux assembly equipped with a condenser and a magnetic bar, and also an oil bath on a hotplate. The reaction mixture was stirred and heated under argon at a temperature of 70° C. for 24 hours, then at 80° C. for 96 hours and then at 90° C. for 1 week until a very dark homogeneous mixture was obtained. The reaction products were precipitated from a large volume of diethyl ether and then filtered off on a Büchner funnel.

The product obtained (BGE-LiAN) was dried under reduced pressure and a red powder was obtained.

Example 11—Preparation of the Liquid Crystal 12-LiAN' in Accordance with the Invention

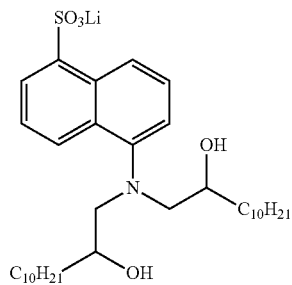

2.903 g (12.67 mmol) of LiAN' and 6.15 g (25.33 mmol) of 1,2-epoxydodecane in 15 mL of dimethylformamide DMF were placed in a 50 mL round-bottomed flask mounted on a reflux assembly equipped with a condenser and a magnetic bar, and also an oil bath on a hotplate. The reaction mixture was stirred and heated under argon at a temperature of 100° C. for 2 weeks until a very dark brown homogeneous mixture was obtained. The reaction products were precipitated from a large volume of diethyl ether and then filtered off on a Büchner funnel.

The product obtained (12-LiAN') was dried under reduced pressure and a red powder was obtained.

The observations by DSC and SAXS confirmed that 12-LiAN' is a thermotropic ionic liquid crystal with an undefined organization between 10° C. and 70° C., and then an organization of lamellar type above 70° C.

Example 12—Preparation of the Liquid Crystal 16-LiAN' in Accordance with the Invention

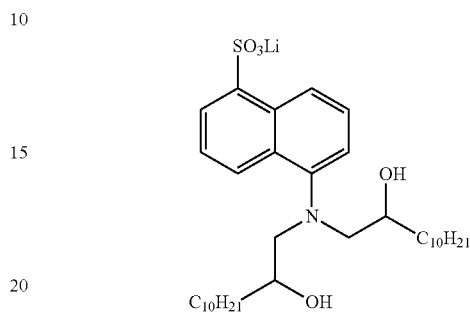

3.160 g (13.79 mmol) of LiAN' and 7.80 g (27.57 mmol) of 1,2-epoxyhexadecane in 25 mL of dimethylformamide DMF were placed in a 100 mL round-bottomed flask mounted on a reflux assembly equipped with a condenser and a magnetic bar, and also an oil bath on a hotplate. The reaction mixture was stirred and heated under argon at a temperature of 90° C. for 2 weeks until a very dark brown homogeneous mixture was obtained. The reaction products were precipitated from a large volume of diethyl ether and then filtered off on a Büchner funnel.

The product obtained (16-LiAN') was dried under reduced pressure and a red powder was obtained.

The observations by DSC and SAXS confirmed that 16-LiAN' is a thermotropic ionic liquid crystal with a columnar organization from room temperature to 80° C., and then a lamellar phase up to 160° C. (clarification temperature).

Example 13—Ion Conductivity Measurements

The measurements were taken between the upper and lower plate of a plate/plate rheometer using disposable geometries in an oven allowing conductivity measurements up to 250° C. The two parallel plates represent the two electrodes of electrochemical impedance spectroscopy measurements and were connected to the working electrode and to the counter-electrodes of an impedance spectrometer.

The test product was placed on the lower geometry and the upper geometry was descended up to an applied force of 5 N. The system was heated to melt the product while maintaining a force of 5 N, so as to ensure a perfect contact surface between the sample and the electrodes. Gradually as the temperature increased, the measurement gap decreased and the value (displayed digitally on the rheometer) was recorded so as to be able to calculate the ion conductivity. Impedance spectroscopy was performed with an amplitude of 10 mV from 1 MHz to 10 MHz for each temperature.

The results obtained are indicated in FIGS. 8 and 9 (ion conductivity in S/cm as a function of 1000, where T is the temperature in kelvins).

The thermotropic ionic liquid crystal molecules in accordance with the invention 12-LiAN, 12-LiAN', 14-LiAN, 16-LiAN and 16-LiAN' have ion conductivity over a broad temperature range, from about $10^{-9}$ S/cm at about 60° C. to about $10^{-5}$ S/cm at about 200° C.

These thermotropic ionic liquid crystal molecules in accordance with the invention are suitable for use as electrolyte in an electrochemical system, in particular in a lithium battery.

The invention claimed is:

1. An electrolyte, comprising a thermotropic ionic liquid crystal molecule, in a mesomorphic state, wherein the molecule comprises:
a rigid part, comprising a polycyclic group Ar formed from 2 to 6 rings, at least one of which is aromatic, the rings being, independently of each other, 4- to 6-membered, the polycyclic group optionally including up to 18 heteroatoms;
a flexible part, formed from one or more linear or branched, saturated or unsaturated, fluorinated or nonfluorinated aliphatic chains, the chain(s) being optionally interrupted with one or more heteroatoms, metalloids, and/or aromatic or nonaromatic, 4- to 6-membered (hetero)cycles, and optionally substituted with one or more hydroxyl, —NH$_2$, and/or oxo groups, the flexible part being covalently bonded, directly or via a spacer, to the rigid part; and
an ionic group -A$^{x-}$C$^{x+}$,
wherein -A$^{x-}$ is an anionic group covalently bonded to the rigid part, with x being an integer equal to 1 or 2, -A$^{x-}$ being a sulfonate anion, sulfonylimide of formula —SO$_2$—N$^-$—SO$_2$C$_y$F$_{2y+1}$ with y being an integer ranging from 0 to 4, borate, borane, phosphate, phosphinate, phosphonate, silicate, carbonate, sulfide, selenate, nitrate, and/or perchlorate, and
wherein C$^{x+}$ is a counter-cation of -A$^{x-}$, and C$^{x+}$ is H$^+$, an alkali metal cation, and/or an alkaline-earth metal cation.

2. The electrolyte of claim 1, wherein, in the molecule, the polycyclic group Ar has one of the following backbones:

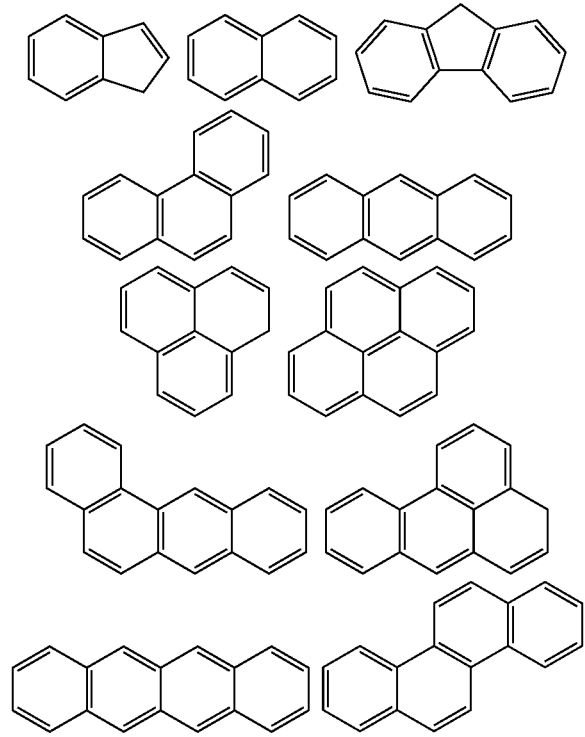

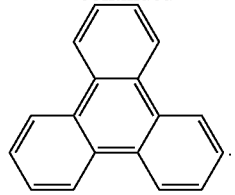

3. The electrolyte of claim 1, wherein, in the molecule, the polycyclic group Ar is an aromatic bicyclic group.

4. The electrolyte of claim 1, wherein, in the molecule, the flexible part is formed from:
a single branched aliphatic chain, comprising a linear sequence of at least 6 covalent bonds; or
at least two linear or branched aliphatic chains, each of the chains comprising a linear sequence of at least 6 covalent bonds.

5. The electrolyte of claim 1, wherein, in the molecule, each of the aliphatic chains is formed from a single chain segment or from a linear sequence of at least two chain segments.

6. The electrolyte of claim 1, wherein, in the molecule, the aliphatic chain(s) forming the flexible part are covalently bonded directly to one or more carbon atoms or heteroatoms of the group Ar forming the rigid part.

7. The electrolyte of claim 1, wherein, in the molecule, the aliphatic chain(s) forming the flexible part are covalently bonded via a spacer to one or more carbon atoms or heteroatoms of the group Ar forming the rigid part.

8. The electrolyte of claim 7, wherein the aliphatic chain(s) are covalently bonded to a carbon atom of the group Ar via an atom of valency greater than or equal to 2.

9. The electrolyte of claim 8, wherein the atom of valency greater than or equal to 2 is a nitrogen atom.

10. The electrolyte of claim 7, wherein, in the molecule, the flexible part is formed from two linear alkyl chains, comprising from 4 to 18 carbon atoms, optionally substituted with one or more hydroxyl groups, optionally interrupted with one or more oxygen atoms,
wherein the chains are bonded to a carbon atom of the group Ar via a nitrogen atom.

11. The electrolyte of claim 1, wherein, in the molecule, the anionic groups -A$^{x-}$ are sulfonate anions and/or anions of formula —SO$_2$—N$^-$—SO$_2$—C$_y$F$_{2y+1}$ with y ranging from 0 to 4.

12. The electrolyte of claim 1, wherein, in the molecule, C$^{x+}$ is H$^+$ or a Li$^+$ cation.

13. The electrolyte of claim 1, wherein the molecule has the structure:

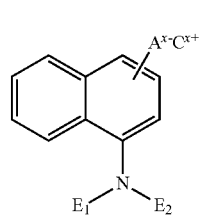

(I)

wherein E$_1$ and E$_2$ represent identical or different linear or branched, saturated or unsaturated, fluorinated or nonfluorinated aliphatic chains, the chain(s) being optionally interrupted with one or more heteroatoms, metalloids, and/or aromatic or nonaromatic, 4- to 6-membered (hetero)cycles, and optionally substituted with one or more groups selected from the group consisting of hydroxyl, —NH$_2$ and oxo groups.

14. The electrolyte of claim 13, wherein the chains $E_1$ and $E_2$ represent identical or different linear alkyl chains, comprising from 6 to 16 carbon atoms, each being substituted with a hydroxyl group, optionally fluorinated, and optionally interrupted with an oxygen atom.

15. The electrolyte of claim 1, having a viscosity of greater than or equal to 10 mPa·s at a temperature of between −60° C. and 300° C.

16. The electrolyte of claim 1, having an ion conductivity at 20° C. of greater than or equal to $10^{-9}$ S/cm, and an ion conductivity at 200° C. of greater than or equal to $10^{-5}$ S/cm.

17. The electrolyte of claim 1, wherein, in the molecule, the polycyclic group Ar is an aromatic bicyclic group with a naphthalene aromatic backbone.

18. The electrolyte of claim 1, wherein, in the molecule, the polycyclic group Ar is a naphthalene group.

19. The electrolyte of claim 1, wherein, in the molecule, each of the aliphatic chains is formed from a linear sequence of two or three chain segments of different chemical nature.

20. The electrolyte of claim 1, wherein, in the molecule, the anionic groups -A$^{x-}$ are sulfonate anions.

21. The electrolyte of claim 1, wherein the molecule comprises:

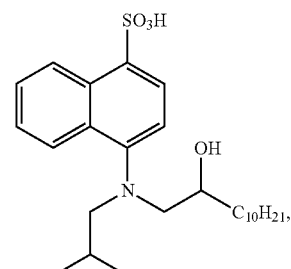

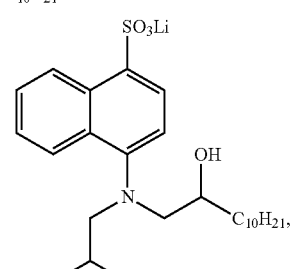

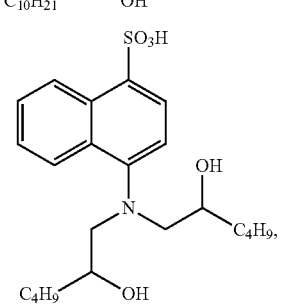

-continued

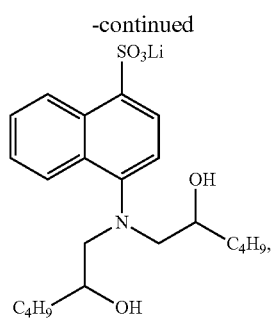

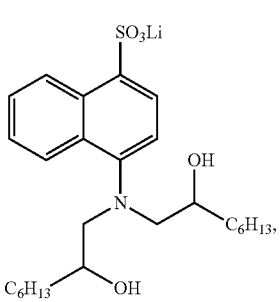

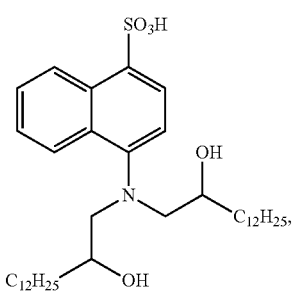

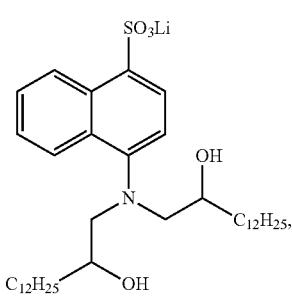

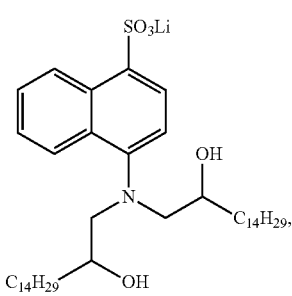

-continued
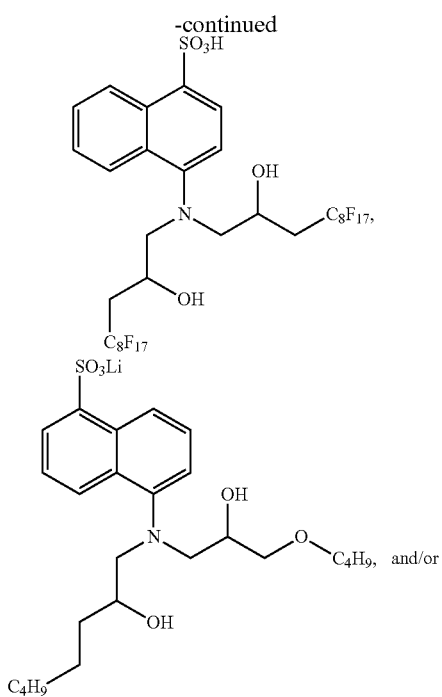
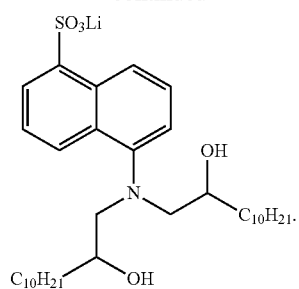
22. An electrochemical system comprising the electrolyte of claim 1.
23. The electrochemical system of claim 22, which is a battery.
24. The electrochemical system of claim 23, wherein the system is a lithium battery.
25. A porous separator, which is impregnated with the electrolyte of claim 1.
* * * * *